United States Patent [19]

Madsen et al.

[11] 4,282,241
[45] Aug. 4, 1981

[54] ORGANIC FLUORO-IMIDES, THEIR PREPARATION AND USE

[75] Inventors: Hans B. Madsen; Per D. Klemmensen; Hans Kolind-Andersen, all of Lemvig, Denmark

[73] Assignee: A/S Cheminova, Lemvig, Denmark

[21] Appl. No.: 115,720

[22] Filed: Jan. 28, 1980

Related U.S. Application Data

[60] Continuation of Ser. No. 967,507, Dec. 7, 1978, abandoned, which is a division of Ser. No. 742,592, Nov. 17, 1976, Pat. No. 4,148,901.

[30] Foreign Application Priority Data

Nov. 25, 1975 [GB] United Kingdom ............... 48441/75
Aug. 25, 1976 [GB] United Kingdom ............... 35820/76

[51] Int. Cl.³ .................. A01N 37/32; C07D 209/48
[52] U.S. Cl. ............................... 424/274; 260/326 H
[58] Field of Search .................. 260/326 S, 326 H; 424/274

[56] References Cited

U.S. PATENT DOCUMENTS

| | | | |
|---|---|---|---|
| 3,036,088 | 5/1962 | Harris, Jr. | 424/274 X |
| 3,178,447 | 4/1965 | Kohn | 424/274 X |
| 3,840,555 | 10/1974 | Baker et al. | 260/326 H X |
| 3,911,134 | 10/1975 | Pommer et al. | 424/274 X |
| 4,148,901 | 4/1979 | Madsen et al. | 260/326 H X |
| 4,219,558 | 8/1980 | Madsen et al. | 260/326 H X |

OTHER PUBLICATIONS

Siegel et al, Anti-Fungal Compounds, vol. 1, pp. v, vi, vii, viii, ix, 399–405, 7 416–417, Marcel Dekker Inc. NY (1977).
Torgeson, Fungicides, vol. 1, frontispage and p. 412, Academic Press NY (1967).
Wegler, Chemie der Pflanzenschutzund Schadlingsbekampfungsmittel, vol. 2, frontispage, p. VI, 25, Springer-Verlag, Berlin (1970).
Pesticide Dictionary, p. D 51, 1979, Farm Chemicals Handbook, Meister Publishing Co., Willoughby, Ohio (1979).

*Primary Examiner*—John D. Randolph
*Attorney, Agent, or Firm*—Bacon & Thomas

[57] ABSTRACT

The invention provides novel fluoro-imides/amides of the formula:

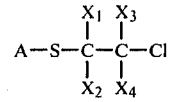

in which at least two of $X_1$, $X_2$, $X_3$ and $X_4$ are fluorine and any of $X_1$, $X_2$, $X_3$ and $X_4$ which is not fluorine, is chlorine, and A is selected from:

(a)

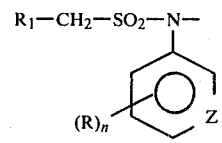

in which
$R_1$ is hydrogen or a halogen atom, preferably chlorine,
Z is CH or a nitrogen atom,
n is 0 or 1, and
R is an alkyl group having 1–6 carbon atoms, preferably methyl, or a halogen atom, preferably chlorine;

(b)

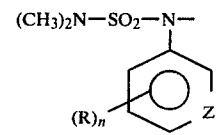

in which Z, n and R have the above-stated meanings;

(c)

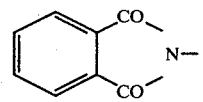

and (d)

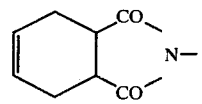

and a process for preparing said compounds.

Said compounds have valuable fungicidal and miticidal activity.

8 Claims, No Drawings

ORGANIC FLUORO-IMIDES, THEIR PREPARATION AND USE

This is a continuation of application Ser. No. 967,507, filed Dec. 7, 1978, now abandoned, which is a division of application Ser. No. 742,592, filed Nov. 17, 1976, now U.S. Pat. No. 4,148,901.

This invention is concerned with compounds havng fungicidal and miticidal activity and, more particularly, with novel compounds which may be generally described as organic fluoro-imides/amides, and with their preparation and use.

We have found that compounds of the formula:

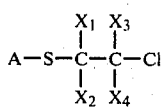
I in which at least two of $X_1$, $X_2$, $X_3$ and $X_4$ are fluorine and any of $X_1$, $X_2$, $X_3$ and $X_4$ which is not fluorine, is chlorine, and A is selected from:

(a)

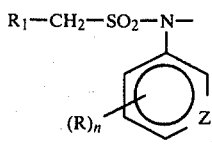

in which
$R_1$ is hydrogen or a halogen atom, preferably chlorine,
Z is CH or a nitrogen atom,
n is 0 or 1, and
R is an alkyl group having 1-6 carbon atoms, preferably methyl, or a halogen atom, preferably chlorine;

(b)

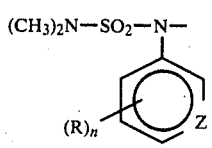

in which Z, n and R have the above-stated meanings;

(c)

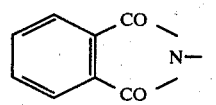

and (d)

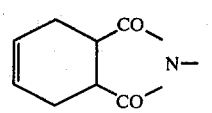

have general activity as fungicides and, in particular, a surprisingly high activity against wood-destroying fungi and fungi which infect grain seeds, and also miticidal activity.

The compounds of formula I are novel and constitute one aspect of the present invention.

Preferred compounds according to the invention are those in which only two of $X_1$, $X_2$, $X_3$ and $X_4$ are fluorine and in which A is (a), (b) or (c) above.

The present invention also comprises a process for the preparation of the compounds of formula I, which comprises condensing a halo-ethyl-thiochloride of the formula:

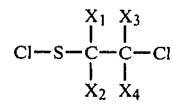

in which $X_1$, $X_2$, $X_3$ and $X_4$ have the above-stated meanings, with an amide or imide selected from:

(a)

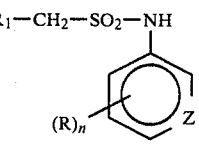

in which $R_1$, Z, n and R have the above-stated meanings;

(b)

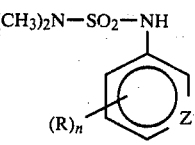

in which Z, n and R have the above-stated meanings;
(c) phthalimide; and
(d) tetrahydrophthalimide of the formula:

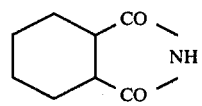

A preferred procedure for carrying out the reaction is to dissolve the appropriate amide/imide in a mixture of chloroform and triethylamine and to this solution slowly add the appropriate halo-ethyl-thiochloride dissolved in chloroform, with stirring. A slightly exothermic reaction takes place and stirring is continued for about 2 hours. The reaction mixture is washed several times with water and then dried over anhydrous $Na_2SO_4$. The dry organic layer is evaporated yielding the desired product nearly quantitatively.

The compounds of the present invention show general fungicidal activity, which is surprisingly high, for example, against discolouring fungi such as *Aspergillus niger* and *Penicillium Spp.*

Accordingly the present invention also includes a composition for the control of fungi or mites which comprises at least one compound of formula I and a suitable carrier.

In addition to their general fungicidal activity, the compounds of the invention also show a surprising high activity against wood-destroying fungi such as *Coniophora cerebella, Polyporus vaporarius* and *Merulius lacrymans.*

Accordingly the present invention also includes a process for preserving wood against fungal attack, which comprises treating the wood with an effective amount of at least one compound of formula I.

Compounds of the present invention also show activity as fungicides against grain seed-attacking fungi, for example those that attack rye, wheat and barley, such as *Urocystis occulta* (stripesmut), *Tilletia caries* (stinking bunt) and *Helinthosporium gramineum* (Barley leaf stripe).

Accordingly the present invention also includes a process and a composition for grain seed dressing for protection against seed-borne diseases.

Compositions of the present invention may be prepared by incorporating one or more compounds of formula I in emulsifiable oils, wettable powders or dusts of the kind normally used in fungicidal compositions for plant protection. Applied in the same way as when used in plant protection, such composition may also be used for the protection of timber, boards and chips during storage.

Preferred compositions of the invention are compositions in a form suitable for treating wood in order to obtain protection against wood-destroying fungi. Such compositions may be prepared by incorporating a compound of formula I in any of the liquids normally used in preparing wood protective compositions, more particularly organic solvents in which the compounds are soluble to the desired concentrations. Suitable organic solvents are, for example, liquid hydrocarbons and mixtures of two or more thereof, preferably liquid aliphatic hydrocarbons, mixtures of two or more thereof, and mixtures of one or more thereof with a minor proportion of one or more liquid aromatic hydrocarbons. It is particularly preferred to use white spirit, kerosene or similar commercial liquid hydrocarbon fractions. Other very suitable solvents are cyclohexanone and tetramethylurea. The concentration of active compound in the composition will usually be from 0.1% to 10% by weight, and preferably from 0.1% to 2%. However, the concentration is not critical and should only be high enough to ensure that protection is obtained by means of the selected type of treatment.

Any suitable process for treating wood may be used and, in particular, any of the conventional processes as described in the technical literature. Suitable treatments include, for example, surface treatments (brushing, immersion, etc.), sap-displacements methods (such as the Boucherie-method), and tank-impregnation methods (such as Rüping's method or Rütger's method). While the above-staged ranges of concentration are generally satisfactory, the concentration of active compound in the treating liquid, and other aspects of the composition of the latter, can be varied as required, depending on such factors as the type of wood, the intended function of the wood, the degree of protection desired and the treatment process. Persons skilled in the art will have no difficulty in determining suitable known compositions and methods of treatment in any particular case.

The composition may, if desired, contain ingredients which serve to bind the active compound to the wood, the addition of such binders being well known in the art. Use may be made, for example, of conventional alkyd-resin binders, linseed oil or other commonly used varnish materials. The concentrations of such binders may vary considerably in accordance with specific requirements, for example, up to 10% by weight or even more. As a suitable composition for treating wood there may be mentioned, by way of example, a liquid composition comprising about 1% by weight of a compound of formula I, 9% by weight of a conventional alkyd-resin binder (or a similar quantity of linseed oil) and 90% by weight of white spirit.

The compounds, the compositions and the processes of the present invention are useful for the protection of all kinds of wood susceptible to the attack of wood-destroying fungi, such as pine, beech, etc., for example, in the form of posts, poles, boards, beams and all kinds of timber for building purposes.

The starting materials used for the preparation of the compounds of formula I are either known or, if they are not, they may be prepared in the same manner as known analogous compounds. By way of example, the halo-ethylenes used for the preparation of the appropriate halo-ethylthiochlorides may be prepared as described in Houben-Weyl, *Methoden der organischen Chemie* (1962), Vol. V, part 3, pages 119–132.

The preparation and use of the compounds of the present invention are further illustrated by the following examples.

EXAMPLE 1

Preparation of N-(2,2-difluoro-1,1,2-trichloroethylthio)-N-phenyl methanesulphonamide. (Compound No. 1)

To a stirred solution of 0.186 mole of N-phenylmethanesulphonamide and 0.204 mole of triethylamine in 400 ml of dry chloroform was slowly added 0.167 mole of 2,2-difluoro-1,2,2-trichloroethyl-1-thiochloride dissolved in 100 ml of dry chloroform. The reaction at room temperature was slightly exothermic. Stirring was continued for about 2 hours. After washing twice with water, the organic layer was separated and dried over anhydrous $Na_2SO_4$, and then evaporated to yield a nearly quantitative amount of the desired product as a crystalline mass, which was recrystallized twice from anhydrous ethyl alcohol yielding white crystals having a melting point of 86.5°–87.0° C. Elemental analysis gave the result:

Calculated: C,29.16%—H,2.18%—Cl,28.70%—N,3.78%—S,17.30%. Found: C,29.36%—H,2.17%—Cl,28.19%—N,3.80%—S,17.72%.

The NMR-spectrum at 60 MHz in $CDCl_3$ with TMS as internal standard displayed a singlet (3 H) at 2.97 ppm ($CH_3$—$SO_2$—) and a singlet (5 H) at 7.40 ppm ($C_6H_5$—M—).

EXAMPLE 2

Using the procedure of Example 1, but with the appropriate changes in the starting materials used, the following compounds were prepared:

Compound No.2: N-(1,2-difluoro-1,2,2-trichloroethylthio)-N-phenyl methanesulphonamide. Mp: 64°–72° C.

Compound No.3: N-(1,2,2-trifluoro-1,2-dichloroethylthio)-N-phenyl methanesulphonamide. Mp: 62.5° C.

Compound No.4: N-(2,2-difluoro-1,1,2-trichloroethylthio)-N-(4-chlorophenyl) methanesulphonamide. Mp: 88.1°–90.1° C.

Compound No.5: N-(2,2-difluoro-1,1,2-trichloroethylthio)-N-(3-chlorophenyl) methanesulphonamide. Liquid.

Compound No.6: N-(2,2-difluoro-1,1,2-trichloroethylthio)-N-(3-pyridyl) methanesulphonamide. Delayed and incomplete crystallization.

Compound No.7: N-(2,2-difluoro-1,1,2-trichloroethylthio)-N-phenyl chloromethanesulphonamide. Mp: 57.5°–59° C.

Compound No.8: N-(2,2-difluoro-1,1,2-trichloroethylthio)-N-(2-methylphenyl) chloromethanesulphonamide. Delayed and incomplete crystallization.

Compound No.9: N,N-dimethyl-N'-(2,2-difluoro-1,1,2-trichloroethylthio)-N'-phenyl sulphamide. Mp: 75.0°–76.3° C.

Compound No.10: N,N-dimethyl-N'-(1,2-difluoro-1,2,2-trichloroethylthio)-N'-phenyl sulphamide. Mp: 65°–67° C.

Compound No.11: N,N-dimethyl-N'-(2,2-difluoro-1,1,2-trichloroethylthio)-N'-(4-methylphenyl) sulphamide. Mp: 72°–74° C.

Compound No.12: N,N-dimethyl-N'-(2,2-difluoro-1,1,2-trichloroethylthio)-N'-(4-chlorophenyl) sulphamide. Liquid.

Compound No.13: N,N-dimethyl-N'-(2,2-difluoro-1,1,2-trichloroethylthio)-N'-(3-pyridyl) sulphamide. Mp: 75.8°–78.8° C.

Compound No.14: N,N-dimethyl-N'-(1,2,2-trifluoro-1,2-dichloroethylthio)-N'-phenyl sulphamide. Mp: 71°–76° C.

EXAMPLE 3

Preparation of N-(halo-ethylthio)-phthalimides

To a suspension of 0.1 mole potassium phthalimide in 200 ml of benzene, there was added a solution of 0.1 mole of the appropriate halo-ethyl-thio-chloride in 50 ml of benzene. The reaction was exothermic and the temperature was maintained below 30° C. After completion of the addition, the mixture was heated to about 70° C. and allowed to stand overnight. The benzene was removed under reduced pressure and the residue dissolved in a mixture of chloroform and water. The chloroform layer was separated, washed twice with a cold aqueous sodium hydroxide and twice with water, dried over sodium sulphate, filtered and stripped. A white solid was formed.

In accordance with this procedure we have prepared:
Compound No.15: N-(2,2-difluoro-1,1,2-trichloroethylthio)phthalimide, Mp: 103°–105° C.

EXAMPLE 4

Preparation of N-(halo-ethylthio)-tetrahydro-phthalimides

A first solution was prepared by mixing together 100 ml of water and 0.05 mole of the appropriate halo-ethylthio-chloride. A second solution containing 0.05 mole of tetrahydrophthalimide and 0.05 mole of sodium hydroxide and 100 ml of water was prepared by mixing the ingredients together. The second solution was added to the first solution over a period of five minutes at 10°–15° C. with stirring and cooling. A solid formed and the mixture was stirred for a further 30 minutes. 100 ml of chloroform was then added. The chloroform solution was dried over magnesium sulphate and evaporated under reduced pressure to yield a slightly yellow oil. On standing, crystals formed. 10 ml of n-pentane was then added and the crystals filtered off and washed with additional n-pentane to yield white crystals.

In accordance with this procedure we have prepared:
Compound No. 16: N-(2,2-difluoro-1,1,2-trichloroethylthio)tetrahydrophthalimide, M.p. 45° C.

Compound No. 17: N-(1,2,2-trifluoro-1,2-dichloroethylthio)tetrahydrophthalimide. White oil.

EXAMPLE 5

Test for general fungicidal activity as shown by activity against *Pullularia pullulans* (P 268) and *Aspergillus niger* (EMPA).

The compound to be tested was dissolved in a suitable solvent, such as dimethylformamide, ethyl acetate or water, and 0.3 ml of the solution was distributed evenly over a piece of filter paper (Whatman No. 40). The area of the paper was 19.5 cm$^2$. After evaporation of the solvent, the paper was placed in a plastic bag which was sealed and radiosterilized. For the test, the paper was placed on an agar medium in a sterilized petri dish and the medium was inoculated with spores of the appropriate fungus. After 10 days of exposure at 29° C. and 85% relative humidity the test dish was inspected. Tests showing no sign of growth on and in a narrow zone around the filter paper were rated as positive.

The following compounds of formula I were tested by this procedure and the following table shows the lowest %age concentration necessary to obtain a positive test.

| Compound No. | Pullularia | Aspergillus |
| --- | --- | --- |
| 1. | 0.005 | 0.005 |
| 2. | 0.005 | 0.0001 |
| 3. | 0.05 | 0.05 |
| 4. | 0.005 | <0.00001* |
| 5. | 0.005 | 0.00005 |
| 6. | 0.5 | 0.5 |
| 7. | 0.005 | 0.0001 |
| 8. | 0.005 | 0.0001 |
| 9. | 0.5 | 0.05 |
| 10. | 0.005 | 0.0005 |
| 11. | 0.005 | 0.0005 |
| 12. | 0.005 | 0.0005 |
| 13. | 0.05 | 0.005 |
| 14. | 0.1 | 0.05 |
| 15. | 0.005 | 0.01 |
| 16. | 0.05 | 0.05 |
| 17. | 0.05 | 0.05 |

*("<" means less than)

In order to make a comparison with known compounds, we have also tested the known fungicidal compounds, N-(2-fluoro-1,1,2,2-tetrachloroethylthio)-N-phenyl methanesulphonamide (Stauffer Chem. Co. R 10044) and N-(1,1,2,2-tetrachloroethylthio)-tetrahydro phthalimide (Difolatan).

For both of these compounds, the concentration required for a positive test using the foregoing procedure was 0.01% for both fungi.

EXAMPLE 6

Test for activity against wood-destroying fungi

The activity against wood-destroying fungi was tested with respect to *Coniophora cerebella*. Samples of pine wood having the dimensions 7 cm × 1.6 cm × 0.2 cm were dried for 24 hours at 103° and then weighed.

A concentration series of 1, 0.5, 0.25 and 0.125% of the compound to be tested was prepared as a solution in white spirit containing 9% of an alkyd binder. The wood samples were impregnated by dipping into one of these solutions for a short time. The wet samples were weighed, the uptake being about 100 kg of the solution per cubic meter of wood. The samples were then dried for two days at room temperature.

Six samples were impregnated with each concentration of the test compound. Three of them were packed in sterilizable plastic bags and radiosterilized by UV or gamma-radiation, and the other three were leached for three days in running water at 20° C., the exchange of water being approximate 6 times per day. After the leaching, they were dried for 2 days at room temperature and then packed and sterilized as mentioned above.

Glass bottles containing 500 ml of soil specially nutrified for the growing of *Coniophora cerebella* were sterilized by autoclaving for 3 hours at 120° C. and then cooled. The wood samples were placed in the bottles, the soil was inoculated with *Coniophora cerebella* and incubation was carried out for 4 weeks at 22° C. and 70% relative humidity.

After incubation, the samples were carefully brushed, then dried at 103° C. and weighed. The weight loss of each sample was calculated as %age of the initial dry weight.

The data given in the following table shows the weight loss (as %age) as the average of 3 samples.

|  |  |  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| Concentration in % | Without leaching | 1.0 | 0 | 0 | 0 | 0 | 0 | >20 | 0 | 0 | 0 | 0 | 0 | 0 | 0 | 0 | 0 | 0 | 0 |
|  |  | 0.5 | 0 | 0 | 0 | 0 | 0 |  | 0 | 0 | 0 | 0 | 0 | 0 | 0 | 0 | 0 | 12 | 10 |
|  |  | 0.25 | 0 | 0 | 12 | 0 | 0 |  | 0 | 1 | 0 | 0 | 0 | 0 | 0 | 8 | 1 | 17 | >20 |
|  |  | 0.125 | 2 | 0 | >20 | 2 | 0 |  | 0 | 8 | 5 | 0 | 0 | 2 | 1 | >20 | 2 | >20 |  |
|  | With leaching | 1.0 | 0 |  | 5 |  |  |  |  | 0 |  |  |  |  |  | 2 | 0 | 10 | 12 |
|  |  | 0.5 | 0 |  | 14 |  |  |  |  | 0 |  |  |  |  |  | 15 | 0 | >20 | >20 |
|  |  | 0.25 | 1 |  | >20 |  |  |  |  | 1 |  |  |  |  |  | >20 | 0 |  |  |
|  |  | 0.125 | 6 |  |  |  |  |  |  | 4 |  |  |  |  |  |  | 1 |  |  |

For the purpose of comparison, the following well known wood protectants were tested in exactly the same way:
α Pentachlorophenol+abietylamine (1/1 molar)
β Pentachlorophenol+tributyltinoxide (1/1 molar)
γ Dichlofluanid The test without leaching gave the following results:

| Conc/Comp. | α | β | γ |
|---|---|---|---|
| 1.0 | 18 | 0 | 1 |
| 0.5 | >20 | 4 | 1 |
| 0.25 |  | 18 | 14 |
| 0.125 |  | >20 | >20 |

As a control 8 tests were carried out with unimpregnated samples; the weight losses were between 18% and 40%.

EXAMPLE 7

Uninfected grain seeds and grain seeds infected with the specified fungi:
Wheat (Kranic) with *Tilletia caries*
Rye (Petkus II) with *Urocystis occulta* and
Barley (Lami) with *Helminthosporium gramineum*
were pretreated and sown in small plots 1 m×0.5 m in Jutland, Denmark.

All seeds were pretreated with an emulsion of olive oil in water and then treated for 5 minutes with a powder, which was either inert or contained either 200 or 2000 ppm of the compound to be tested. The compounds tested were three compounds according to the invention, three other compounds for the purpose of comparison, and mercury at the rate of 20 ppm. The wheat and rye were sown in mid-October 1975 and the barley in mid-March 1976. The plots were inspected in early August 1976 and the number of individual plants up to and including 10 that were infected with fungal disease, was noted (where more than 10 individual plants were infected, the result is recorded in the following table as ">10").

The results obtained are shown in the following Table; each result is the average of a number of identically sown plots.

| Compound | Wheat 200 ppm | Wheat 2000 ppm | Rye 200 ppm | Rye 2000 ppm | Barley 200 ppm | Barley 2000 ppm |
|---|---|---|---|---|---|---|
| 3 | >10 | 7.5 | >10 | 3 | >10 | 5 |
| 4 | >10 | >10 | >10 | 5 | >10 | >10 |
| 17 | >10 | >10 | >10 | 2 | >10 | 8.5 |
| CH₃—S(O)₂—N(—C₆H₅)—S—CCl₂—CCl₂F | >10 | >10 | >10 | 3.5 | >10 | >10 |
| (phthalimide)N—S—CCl₂—CCl₂F | >10 | >10 | >10 | 4.5 | >10 | 9.5 |
| (phthalimide)N—S—CCl₂—CHCl₂ | >10 | >10 | >10 | >10 | >10 | >10 |

| Controls | Wheat | Rye | Barley |
|---|---|---|---|
| Infected, untreated | >10 | >10 | >10 |
| Uninfected, untreated | 3.3 | 0 | 0 |
| 20 ppm mercury on infected seeds | 5.5 | 0 | 0.5 |

EXAMPLE 8

The fungicidal and miticidal activities of Compound 1 according to the invention in the treatment of apple trees was tested and compared with those of an analogous compound, N-(2-fluoro-1,1,2,2-tetrachloroethylthio)-N-phenyl methanesulphonamide (Stauffer Chemical Co; Compound R-10044) and three commercially available plant-protection compounds, maneb (Dithane), captan (Orthocid) and binapacryl.

Cox Orange Pippin, Golden Delicious and Cortland apple trees were sprayed with aqueous dispersions of the following.

| Name | Code/synonym | Chemical structure |
|---|---|---|
| | R-10044 | 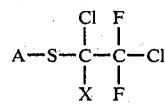 |
| Compound 1 | HKA-3 | 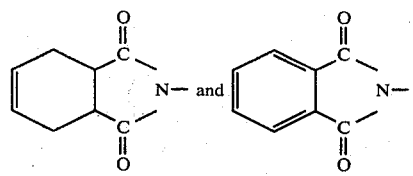 |
| Dithane | maneb | 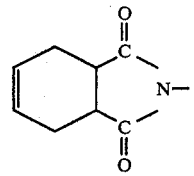 |
| Orthocid | captan | 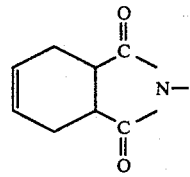 |
| binapacryl | | 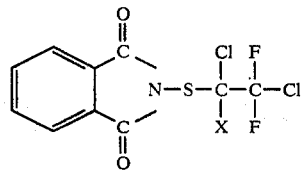 |

Each compound was applied at the rate of 0.2, 0.6 and 2 kilograms of active ingredient per hectare. Each variation of the spraying programme was performed on five trees.

No trees in the experiment, including those which were untreated, had attacks of apple scab (*Venturia inaequalis*).

All trees treated with Compound 1 (HKA-3) and R-10044 were attacked by mildew. Compound 1 applied at 2 kg. a.i./ha showed somewhat weaker attacks of mildew, as compared to the mildew attacks in untreated trees.

Infestations of spider mites (*Tetranychus urticae*) were observed as indicated in the following table:

| | dosage (kg a.i./ha) | | |
|---|---|---|---|
| Compound applied | 2.0 | 0.6 | 0.2 |
| R-10044 | no attack | few mites | attack |
| Compound 1 (HKA-3) | no attack | no attack | no attack |
| Dithane/maneb | attack | attack | attack |
| Orthocid/captan | attack | attack | attack |
| Binapacryl | no attack | few mites | attack |

No difference in results were observed in the different sorts of apples.

The table shows that Compound 1 (HKA-3) provides a better protection against infestations by spider mites than does the recognized miticide, binapacryl.

What is claimed is:

1. A method for protecting non-living wood from fungal attack comprising the step of treating said non-living wood with an effective amount of a compound of the formula:

$$A-S-\underset{X}{\overset{Cl}{\underset{|}{C}}}-\underset{F}{\overset{F}{\underset{|}{C}}}-Cl$$

wherein X is selected from the group consisting of chlorine or fluorine, and A is selected from the group consisting of

[structures shown] and

2. The method of claim 1, wherein X is chlorine and A is

[structure shown]

3. The method of claim 1, wherein X is fluorine and A is

[structure shown]

4. The method of claim 2 or 3, wherein said fungal attack is caused by a fungus selected from the group consisting of a wood discoloring fungus and a wood destroying fungus.

5. A compound of the formula

[structure shown]

wherein X is selected from the group consisting of chlorine and fluorine.

6. A method for protecting non-living wood from fungal attack as defined in claim 1 comprising the step of treating said wood with an effective amount of a compound of the formula

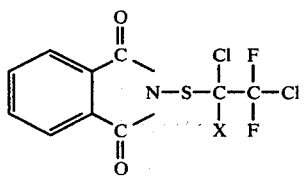
wherein X is selected from the group consisting of chlorine and fluorine.
7. The method of claim 6 wherein X is chlorine and said fungal attack is caused by a wood discoloring fungus.
8. The method of claim 6 wherein X is chlorine and said fungal attack is caused by a wood destroying fungus.
* * * * *